(12) United States Patent
Woodcock et al.

(10) Patent No.: US 11,969,546 B2
(45) Date of Patent: Apr. 30, 2024

(54) MOUTHPIECE

(71) Applicant: NICOVENTURES TRADING LIMITED, London (GB)

(72) Inventors: Dominic Woodcock, London (GB); Ugurhan Yilmaz, London (GB)

(73) Assignee: NICOVENTURES TRADING LIMITED, London (GB)

( * ) Notice: Subject to any disclaimer, the term of this patent is extended or adjusted under 35 U.S.C. 154(b) by 591 days.

(21) Appl. No.: 16/316,282

(22) PCT Filed: Jul. 5, 2017

(86) PCT No.: PCT/EP2017/066802
§ 371 (c)(1),
(2) Date: Jan. 8, 2019

(87) PCT Pub. No.: WO2018/011037
PCT Pub. Date: Jan. 18, 2018

(65) Prior Publication Data
US 2021/0282454 A1    Sep. 16, 2021

(30) Foreign Application Priority Data

Jul. 14, 2016   (GB) ...................................... 1612231

(51) Int. Cl.
*A61M 15/06*    (2006.01)
*A24F 7/00*     (2006.01)
(Continued)

(52) U.S. Cl.
CPC ............... *A61M 15/06* (2013.01); *A24F 7/00* (2013.01); *A24F 40/20* (2020.01); *A24F 40/30* (2020.01);
(Continued)

(58) Field of Classification Search
CPC .................................. A24F 40/20; A24F 40/30
See application file for complete search history.

(56) References Cited

U.S. PATENT DOCUMENTS 4,677,992 A    7/1987   Bliznak
4,889,114 A *  12/1989  Kladders ........... A61M 15/0028
                                                    128/203.15
(Continued)

FOREIGN PATENT DOCUMENTS

CA      2244210      4/2016
CN      103929988 A  7/2014
(Continued)

OTHER PUBLICATIONS

Barry Green, Heat as a Factor in Perception of Taste, Smell, and Oral Sensation, 1993, Institute of Medicine Committee on Military Nutrition Research (Year: 1993).*
(Continued)

*Primary Examiner* — Anthony Calandra
(74) *Attorney, Agent, or Firm* — Husch Blackwell LLP (57) ABSTRACT

A mouthpiece for an apparatus for generating an inhalable medium is disclosed. The mouthpiece defines an aperture extending from a first opening at a first end of the mouthpiece to a second opening at an opposing end of the mouthpiece. The mouthpiece is arranged to receive in the aperture through the first opening a flavor element for imparting a flavor to a flow of at least one of a vapor and an aerosol that passes through the mouthpiece in use. The aperture has a first radial dimension towards the first opening, and a second radial dimension towards the second opening, wherein the second radial dimension is smaller than the first radial dimension.

12 Claims, 7 Drawing Sheets

(51) Int. Cl.
  *A24F 40/20* (2020.01)
  *A24F 40/30* (2020.01)
  *A24F 40/40* (2020.01)
  *A24F 40/42* (2020.01)
  *A24F 40/485* (2020.01)
  *A24F 40/10* (2020.01)

(52) U.S. Cl.
  CPC .............. *A24F 40/40* (2020.01); *A24F 40/42* (2020.01); *A24F 40/485* (2020.01); *A24F 40/10* (2020.01)

(56) References Cited

U.S. PATENT DOCUMENTS

| | | | |
|---|---|---|---|
| 2008/0053465 A1* | 3/2008 | Tarora | A24F 13/06 131/202 |
| 2013/0192615 A1 | 8/2013 | Tucker et al. | |
| 2013/0192620 A1 | 8/2013 | Tucker | |
| 2013/0333709 A1 | 12/2013 | Shimizu | |
| 2014/0166029 A1 | 6/2014 | Weigensberg et al. | |
| 2014/0290650 A1 | 10/2014 | Ivey | |
| 2014/0338686 A1 | 11/2014 | Plojoux | |
| 2015/0027454 A1* | 1/2015 | Li | A24D 3/061 131/328 |
| 2015/0027462 A1 | 1/2015 | Qiuming | |
| 2015/0216232 A1 | 8/2015 | Bless | |
| 2015/0351456 A1 | 12/2015 | Johnson | |
| 2016/0095357 A1 | 4/2016 | Burton | |
| 2016/0198770 A1* | 7/2016 | Alarcon | A24F 40/46 392/404 |
| 2016/0206004 A1* | 7/2016 | Shinkawa | A24F 40/30 |
| 2018/0168224 A1 | 6/2018 | Naughton | |

FOREIGN PATENT DOCUMENTS

| | | | | |
|---|---|---|---|---|
| CN | 203748668 | | 8/2014 | |
| EP | 2984952 | | 2/2016 | |
| EP | 3020291 | | 5/2016 | |
| EP | 3020292 | | 5/2016 | |
| GB | 1033818 | A * | 6/1966 | |
| GB | 2497536 | A | 6/2013 | |
| JP | 10004946 | | 1/1998 | |
| JP | H104946 | A | 1/1998 | |
| JP | 11178563 | | 7/1999 | |
| JP | H11178563 | A | 7/1999 | |
| KR | 101022546 | B1 * | 3/2011 | ............ A24B 15/00 |
| KR | 20120074625 | | 7/2012 | |
| KR | 20150005514 | A | 1/2015 | |
| RU | 2403835 | C2 | 11/2010 | |
| WO | 0028844 | A1 | 5/2000 | |
| WO | 2006098171 | A1 | 9/2006 | |
| WO | WO 2007/123046 | | 11/2007 | |
| WO | WO 2007/123046 | A1 | 9/2009 | |
| WO | WO 2016/079152 | A1 | 5/2016 | |
| WO | WO 2016079152 | | 5/2016 | |
| WO | WO 2016135959 | | 9/2016 | |

OTHER PUBLICATIONS

English Machine translation of WO2007123046 (Year: 2007).*
Second espacenet translation of YULL reference, Dec. 3, 2022. (Year: 2022).*
"Light" Cigarettes and Cancer Risk, 2010, NIH National Cancer Institute. (Year: 2010).*
Japanese Office Action, Application No. 2019-500591, dated Feb. 18, 2020.
Great Britain Search Report, Application No. GB1612231.9, dated Nov. 18, 2016, 4 pages.
Great Britain Search Report, Application No. GB1612231.9, dated Jan. 30, 2017, 3 pages.
Great Britain Search Report, Application No. GB1612231.9, dated Jan. 30, 2017, 4 pages.
International Search Report and Written Opinion, Application No. PCT/EP2017/066802, dated Jan. 17, 2018, 17 pages.
Chinese Office Action for Application No. 201780041118.0, dated Nov. 27, 2020, 8 pages (No translation).
Malaysian Substantive Examination Report for Application No. PI2018002884, dated May 21, 2021, 3 pages.
International Preliminary Report on Patentability for Application No. PCT/EP2017/066802, dated Jan. 24, 2019, 10 pages.
Office Action for Australian Application No. 2020204124, dated Aug. 20, 2021, 3 pages.
Office Action For Chinese Application No. 201780041118.0, dated Aug. 11, 2021, 16 pages.
Office Action For Korean Application No. 10-2019-7004323, dated Apr. 16, 2021, 12 pages.
Office Action dated Feb. 18, 2020 for Japanese Application No. 2019-500591, 14 pages.
Office Action for Brazilian Application No. 112019000651-6, dated Sep. 28, 2021, 4 pages.
Office Action for Chinese Application No. 201780041118.0, dated Feb. 9, 2022, 7 pages.
Notice to File a Response dated May 30, 2022 for Korean Application No. 10-2022-7001978, 40 pages.
"Examination Report received for Australian Patent Application No. 2022224875, dated Aug. 30, 2023", 3 pages.
"Invitation to Pay Additional Fees received for PCT Patent Application No. PCT/EP2017/066802, dated Nov. 6, 2017", 8 pages.
"Office Action received for Brazilian Patent Application No. 112019000651-6, dated Jul. 21, 2023", 4 pages (Official Only).
"Office Action received for Korean Patent Application No. 10-2023-7024579, dated Nov. 7, 2023", 5 pages (2 pages of English Translation and 3 pages of Official).
"Office Action received for Malaysian Patent Application No. PI2021004101, dated Aug. 29, 2023", 3 pages.
"Office Action received for Russian Patent Application No. 2020102266, dated Jul. 19, 2023", 12 pages (5 pages of English Translation and 7 pages of Official).
"Reasons for Refusal received for Japanese Patent Application No. 2021-010574, dated Nov. 8, 2022", 5 pages (2 pages of English Translation and 3 pages of Official Only).

* cited by examiner

MOUTHPIECE

PRIORITY CLAIM

The present application is a National Phase entry of PCT Application No. PCT/EP2017/066802, filed Jul. 5, 2017, which claims priority from GB Patent Application No. 1612231.9, filed Jul. 14, 2016, each of which is hereby fully incorporated herein by reference.

TECHNICAL FIELD

The present disclosure relates to a mouthpiece, and more particularly to a mouthpiece for an apparatus for generating an inhalable medium.

BACKGROUND

Smoking articles such as cigarettes, cigars and the like burn tobacco during use to create tobacco smoke. Attempts have been made to provide alternatives to these articles that burn tobacco by creating products that release compounds without burning.

Examples of such products are heating devices which release compounds by heating, but not burning, the material. The material may be for example tobacco or other non-tobacco products, which may or may not contain nicotine. As another example, there are so-called e-cigarette devices. These devices typically contain a liquid which is heated to vaporize the liquid to produce an inhalable vapor or aerosol. The liquid may contain nicotine and/or flavorings and/or aerosol-generating substances, such as glycerol. The known e-cigarette devices typically do not contain or use tobacco.

SUMMARY

According to a first aspect of the present disclosure, there is provided a mouthpiece for an apparatus for generating an inhalable medium, the mouthpiece defining an aperture extending from a first opening at a first end of the mouthpiece to a second opening at an opposing end of the mouthpiece, the mouthpiece being arranged to receive in the aperture through the first opening a flavor element for imparting a flavor to a flow of at least one of a vapor and an aerosol that passes through the mouthpiece in use, the aperture having a first radial dimension towards the first opening, and a second radial dimension towards the second opening, wherein the second radial dimension is smaller than the first radial dimension.

The second radial dimension may be arranged to prevent the flavor element received in the aperture through the first opening in use from passing through to the second opening.

The aperture may be or comprise a stepped bore, the stepped bore comprising a first bore portion having the first radial dimension and a second bore portion having the second radial dimension.

A step of the stepped bore may be arranged to prevent the flavor element from passing to the second opening.

At least a portion of the stepped bore towards the first opening may be cylindrical.

In use, a step of the stepped bore may support the flavor element received in the aperture through the first opening.

The mouthpiece maybe arranged such that the flavor element received in the aperture through the first opening protrudes beyond the first opening in use.

The first opening may be at a mouth end of the mouthpiece, and the second opening may be at an apparatus end of the mouthpiece.

The mouthpiece may comprise, at the second opening, a chamfer for engaging with a component of the apparatus.

The first opening may be at an apparatus end of the mouthpiece, and the second opening may be at a mouth end of the mouthpiece.

The mouthpiece may comprise, at the first opening, a chamfer for engaging with a component of the apparatus.

The apparatus end of the mouthpiece may be arranged to be releasably connectable to the apparatus.

The mouthpiece may be arranged such that the flavor element, when received in the aperture through the first opening, in use, is removable from and/or replaceable in the aperture through the first opening.

The mouthpiece may comprise the flavor element received in the aperture through the first opening.

A cross section of the flavor element may match a cross section of the aperture.

The flavor element may be one or more of: self-supporting, porous, and cylindrical, and/or comprises a cylindrical portion.

The flavor element may be or comprise tobacco.

The flavor element may protrude beyond the first opening.

The flavor element may be arranged to define a flow path, for the flow of at least one of an aerosol and a vapor, running from one end of the element to another.

According to a second aspect of the present disclosure, there is provided an apparatus for generating an inhalable medium, the apparatus comprising the mouthpiece according to the first aspect.

The flavor element may be received in the aperture through the first opening of the mouthpiece, and the apparatus may comprise: a container for holding a liquid; a heater for volatilizing liquid held in the container to generate the flow of at least one of a vapor and an aerosol in use; and in use the flow of at least one of a vapor and an aerosol may pass through the flavor element for inhalation by a user.

The flavor element may comprise one or more constituents, and in use the flow of at least one of a vapor and an aerosol through the element may entrain one or more of the constituents in the flow.

The first opening of the mouthpiece may be at an apparatus end of the mouthpiece, and the container for holding liquid may comprise a recess into which the element is received.

According to a third aspect of the present disclosure there is provided a mouthpiece for an apparatus for generating an inhalable medium, the mouthpiece defining an aperture extending from a first opening at a mouth end of the mouthpiece to a second opening at an opposing, apparatus end of the mouthpiece, the mouthpiece being arranged to receive in the aperture a flavor element for imparting a flavor to a flow of at least one of a vapor and an aerosol that passes through the mouthpiece in use, the mouthpiece being arranged such that in use the flavor element received into the aperture protrudes beyond the first opening for receipt into a user's mouth, and protrudes beyond the second opening for contact with a component of said apparatus.

The apparatus end of the mouthpiece may be arranged to be releasably connectable to the apparatus.

The mouthpiece may comprise, at the second opening, a chamfer for contacting with said component of the apparatus.

The mouthpiece may be arranged to allow the flavor element, when received in the aperture, to be removed from and/or replaced in the aperture.

The mouthpiece may comprise the flavor element received in the aperture.

The flavor element may protrude beyond the first opening and may protrude beyond the second opening.

A cross section of the flavor element may match a cross section of the aperture.

The flavor element may be one or more of: self-supporting, porous, cylindrical, and/or comprise a cylindrical portion.

The flavor element may be or comprise tobacco.

The flavor element may be arranged to define a flow path, for the flow of at least one of an aerosol and a vapor, running from one end of the element to the other.

According to a fourth aspect of the present disclosure there is provided an apparatus for generating an inhalable medium, the apparatus comprising the mouthpiece according to the third aspect.

The flavor element may be received in the aperture of the mouthpiece, and the apparatus may comprise: a container for holding a liquid; a heater for volatilizing liquid held in the container to generate the flow of at least one of a vapor and an aerosol in use; and in use the flow of at least one of a vapor and an aerosol may pass through the flavor element for inhalation by a user.

The flavor element may comprise one or more constituents, and in use the flow of at least one of a vapor and an aerosol through the flavor element may entrain one or more of the constituents in the flow.

The container for holding liquid may comprise a recess into which the element is received.

According to a fifth aspect of the present disclosure, there is provided a mouthpiece for an apparatus for generating an inhalable medium, the mouthpiece defining an aperture for receiving a flavor element for imparting a flavor to a flow of at least one of a vapor and an aerosol that passes through the mouthpiece in use, the aperture extending from a first opening at a mouth end of the mouthpiece to a second opening at an opposing, apparatus end of the mouthpiece, the mouthpiece comprising, at the second opening, a chamfer for contacting with a component of said apparatus thereby to form a seal between said component and the mouthpiece.

The apparatus end of the mouthpiece may be arranged to be releasably connectable to the apparatus.

The second opening may be circular.

The mouthpiece may be arranged such that the flavor element, when received in the aperture, is removable from and/or replaceable in the aperture.

The mouthpiece may comprise the flavor element received in the aperture.

A cross section of the flavor element may match a cross section of the aperture.

The flavor element may be one or more of: self-supporting, porous, cylindrical, and/or comprise a cylindrical portion.

The flavor element may be or comprise tobacco.

The flavor element may be arranged to define a flow path, for the flow of at least one of an aerosol and a vapor, running from one end of the flavor element to the other.

According to a sixth aspect of the present disclosure, there is provided an apparatus comprising the mouthpiece according to the fifth aspect; and a container for holding a liquid, wherein a rim of the container contacts the chamfer of the mouthpiece thereby to form a seal between the container and the mouthpiece.

The container may comprise a recess for receiving the flavor element.

The apparatus may comprise: a heater for volatilizing liquid held in the container to generate the flow of at least one of a vapor and an aerosol in use; and in use the flow of at least one of a vapor and an aerosol may pass from an outlet of the container into the aperture via the second opening of the mouthpiece.

The flavor element may be received in the aperture, and in use the flow of at least one of a vapor and an aerosol may pass from the outlet of the container into a user's mouth via the flavor element.

The flavor element may comprise one or more constituents, and in use the flow of at least one of a vapor and an aerosol may flow through the flavor element thereby to entrain one or more of the constituents in the flow.

BRIEF DESCRIPTION OF THE DRAWINGS

Further features and advantages will become apparent from the following description of embodiments of the disclosure, given by way of example only, which is made with reference to the accompanying drawings.

FIG. 2b shows a section through line P-P of the exemplary mouthpiece and portion of an apparatus for generating an inhalable medium of FIG. 2a.

FIG. 2c shows a plan view of the exemplary mouthpiece and portion of an apparatus for generating an inhalable medium of FIG. 2a.

FIG. 3b shows a section through line Q-Q of the exemplary mouthpiece and portion of an apparatus for generating an inhalable medium of FIG. 3a.

FIG. 3c shows a plan view of the exemplary mouthpiece and portion of an apparatus for generating an inhalable medium of FIG. 3a.

FIG. 4b shows a section through line R-R of the exemplary mouthpiece and portion of an apparatus for generating an inhalable medium of FIG. 4a.

FIG. 4c shows a plan view of the exemplary mouthpiece and portion of an apparatus for generating an inhalable medium of FIG. 4a.

DETAILED DESCRIPTION

Figure 1:
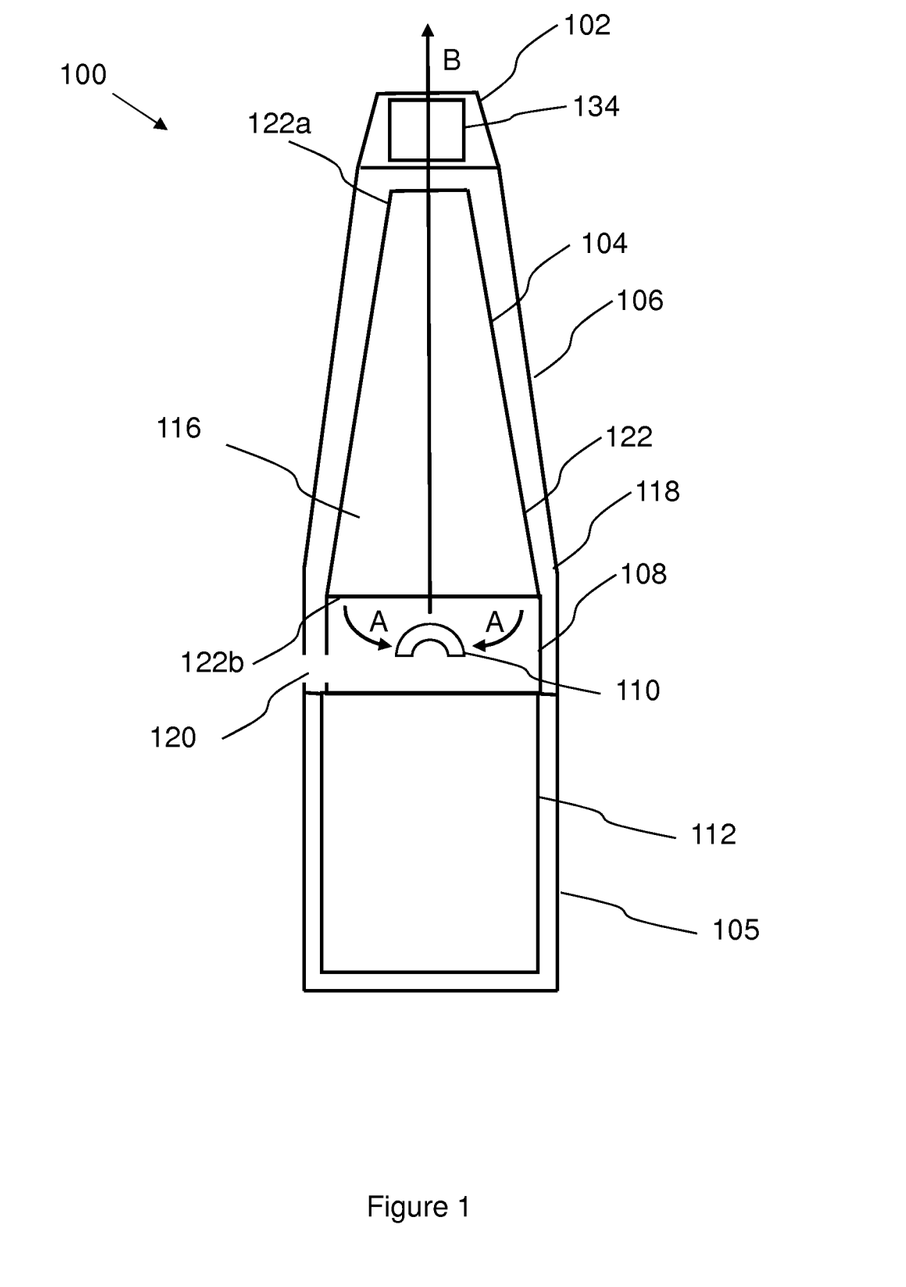
FIG. 1 shows a schematic of an exemplary apparatus for generating an inhalable medium.

Referring to FIG. 1, a schematic of an example apparatus 100 for generating an inhalable medium is illustrated. In this example, the apparatus 100 is a so called "electronic cigarette" device 100. In broad outline, the device 100 volatilizes a liquid to form a vapor or an aerosol which passes through a flavor element 134 received in a mouthpiece 102 of the device 100. The flavor element 134 imparts a flavor to the vapor or aerosol passing through the mouthpiece 102 for inhalation by a user.

In this respect, first it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A colloid is a substance in which microscopically dispersed insoluble particles are suspended throughout another substance.

Returning to FIG. 1, the device 100 comprises an outer body 118 comprising an upper portion 106 housing a cartridge 104 and lower portion 105 housing a battery portion 112. The cartridge 104 is connected to, but removable from, the battery portion 112. At least the upper portion 106 of the outer body 118 may be removed so as to expose the cartridge 104, and hence allow installation, removal and/or replacement of the cartridge 104. The cartridge 104 has a liquid container 122 for containing liquid 116.

The device 100 has a mouthpiece 102 (examples of which are described in more detail below) removeably connected to the upper portion 106 of the outer body 118. The mouthpiece 102 has received therein a flavor element 134 for imparting a flavor to a flow of aerosol or vapor that passes through the mouthpiece 102. The flavor element 134 may be or comprise for example tobacco, or other flavored materials that may be used to create a desired taste or aroma, or other properties, such as nicotine content.

The device 100 is arranged so that as the liquid 116 is volatilized so as to produce an aerosol of liquid droplets or sufficiently heated to produce a vapor, at least some and in some embodiments all or substantially all of the aerosol or vapor passes through the flavor element 134 received in the mouthpiece 102 for example so as to entrain constituents of the flavor element 134 therein.

The liquid container 122 is provided generally centrally of the cartridge 104. The liquid container 122 is frustoconical in shape, but may have a different shape, such as conical, cylindrical, etc. The liquid container 122 is annular in shape and defines a cylindrical channel (not shown) running through the length of the liquid container 122. The liquid container 122 may be formed of rigid, watertight and airtight materials, such as metal, suitable plastics, etc.

The cartridge 104 is provided with a heater 110 and a wick (not shown) in (thermal) contact with the heater 110. In this example, the heater 110 and the wick are provided as a single unit 108, sometimes known as an "atomizer" 108. In this case, where the cartridge 104 includes an atomizer 150, such a cartridge 104 is often referred to as a "cartomizer" 104. The orientation of the heater 110 is shown schematically and for example the heater 110 may be a coil having its longitudinal axis perpendicular or parallel to the longitudinal axis of the cartridge 104. The wick (not shown) is in contact with the liquid 116. This may be achieved for example by the wick (not shown) being inserted through a through hole (not shown) in an end wall 122b of the liquid container 122. Alternatively or additionally, the end wall 122b may be a porous member which allows liquid to pass through from the liquid container 122, and the wick (not shown) may be in contact with the porous end wall 122b. The end wall 122b may be for example in the form of a porous ceramic disk. A porous end wall 122b of this type helps to regulate the flow of liquid onto the wick (not shown). The wick (not shown) is generally absorbent and acts to draw in liquid 116 from the liquid container 122 by capillary action (shown in FIG. 1 by arrows A). The wick can be non-woven and may be for example a cotton or wool material or the like, or a synthetic material, including for example polyester, nylon, viscose, polypropylene or the like, or a ceramic material.

The cartridge 104 is (electrically) connected to a battery in the battery portion 116 to enable the heater 110 to be powered. When the heater 110 is powered (which may be instigated for example by the user operating a button (not shown) of the device 100 or by a puff detector (not shown) of the overall device 100, as is known per se), liquid 116 is drawn (shown in FIG. 1 by arrows A) in from the liquid container 122 by the wick and is heated by the heater 110 to volatilize or vaporize the liquid, so as to generate at least one of a vapor and an aerosol. As the user draws on the mouthpiece 102, air is drawn through an air inlet 120. The liquid 116 is volatilized or vaporized by the heater 110 into air from the air inlet 120 thereby to produce a flow of one of a vapor and an aerosol. The flow vapor or aerosol is drawn through a channel (not shown) of the liquid container 122, through the flavor element 134 received in the mouthpiece 102, and out from the device 100 for inhalation by a user (shown by arrow B in FIG. 1). The vapor or aerosol picks up (entrains) flavor (and/or other constituents) from the flavor element 134. One or more constituents of the flavor element is thereby mixed with the flow of at least one of a vapor and an aerosol. In examples where the flavor element 134 contains or includes nicotine, the vapor or aerosol may also contain nicotine entrained from that solid material. A one-way valve (not shown) may be provided, for example at or near an upper end 122a of the liquid container 122, so that the vapor or aerosol can only exit the cartridge 104 and cannot back-flow to the heater 110 or the electronics (not shown) of the device 100.

The flavor element 134 may be or comprise material that may be used to impart a flavor (and/or one or more other constituents) to the aerosol or vapor. In some examples, the one or more constituents of the flavor element may comprise constituents inherent to the material itself. The material may for example consist of or comprise tobacco. As the aerosol or vapor passes through and over the tobacco, the aerosol or vapor entrains organic and other compounds or constituents from the tobacco that lend tobacco its organoleptic properties, thus imparting the flavor to the aerosol or vapor. It will be understood however that materials other than tobacco may be used to impart different flavors (and/or one or more other constituents) to the aerosol or vapor flow. The flavor element 134 may comprise constituents added to a material of the flavor element 134.

Nicotine may be provided in the liquid 116. Accordingly, where it is intended that the device 100 provides nicotine for the user, the nicotine may be provided in the liquid 116, may be obtained from the flavor element 134, or any combination of these. Likewise, flavorings may be added to the flavor element 134 (whether or not the flavor element 134 is or includes tobacco) and/or to the liquid 116. A material of the flavor element 134 may be a solid material, or be a mixture of solid materials, one or more of each comprising one or more constituents that can be mixed with the flow of vapor or aerosol. It will be appreciated that the flavor element 134 may comprise one or more other constituents that are not entrained into the aerosol or vapor passing there through.

The flavor element 134 may be porous 134, for example so as allow vapor or aerosol to pass through it. The flavor element 134 may be self-supporting, for example the flavor element 134 may comprise material wrapped partially or wholly in a wrapper, and/or the flavor element 134 may be supported in a resilient housing, for example a plastic housing (not shown). The flavor element 134 may be arranged to define a flow path, for a flow of at least one of the aerosol and the vapor, running from one end of the flavor element 134 to another. The flavor element 134 may be cylindrical, and/or comprise a cylindrical portion, for example so as to be received snuggly in a correspondingly shaped hole in the mouthpiece 102.

Figure 2A:
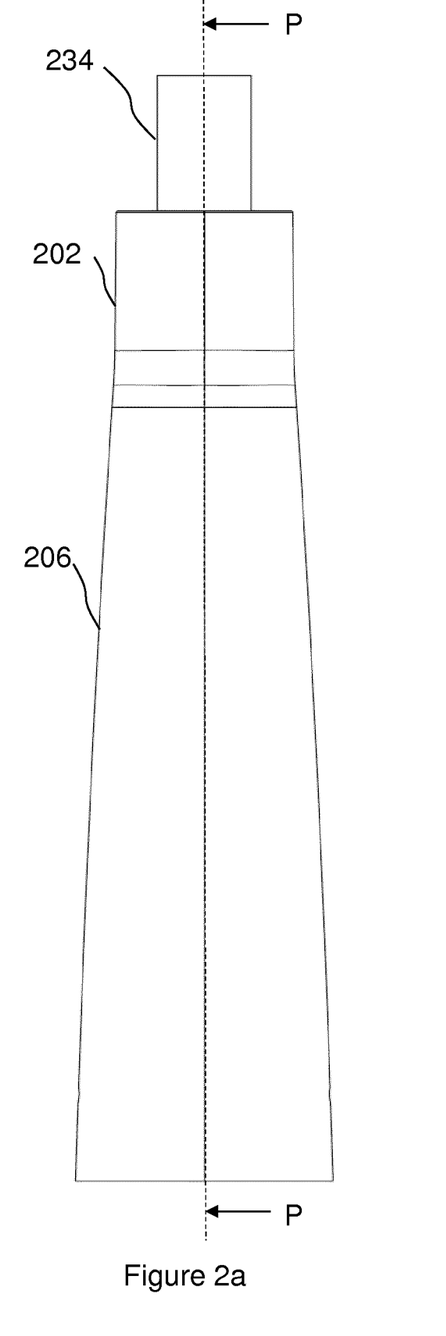
FIG. 2a shows a side view of an exemplary mouthpiece and portion of an apparatus for generating an inhalable medium.
Figure 2B:
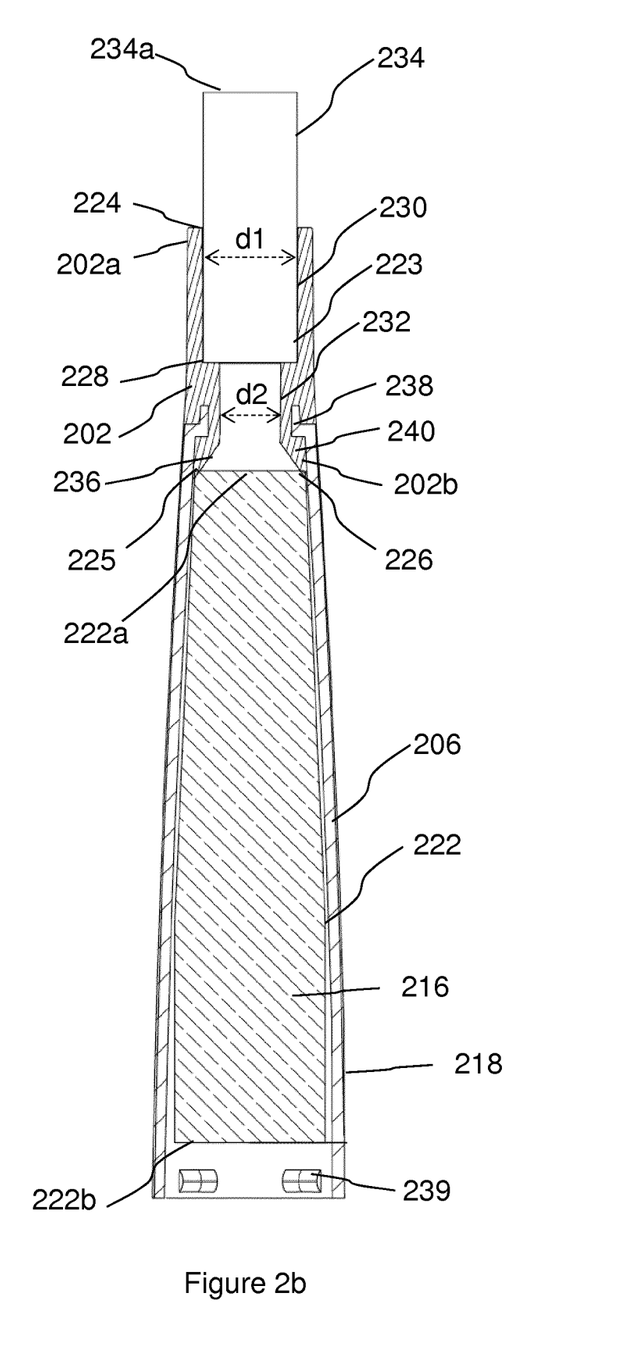
Figure 2C:
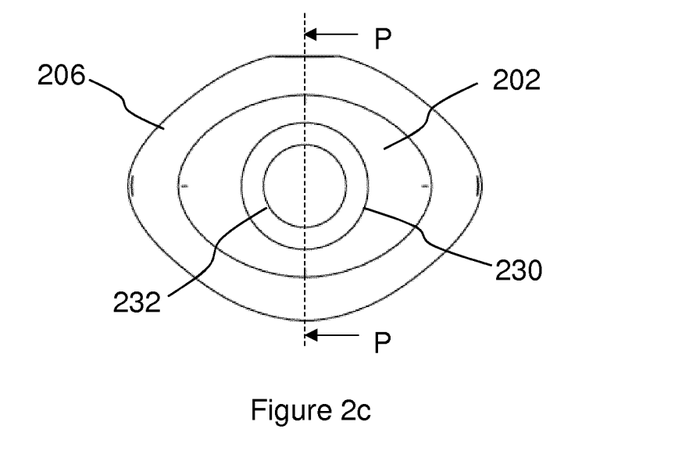
Figure 2D:
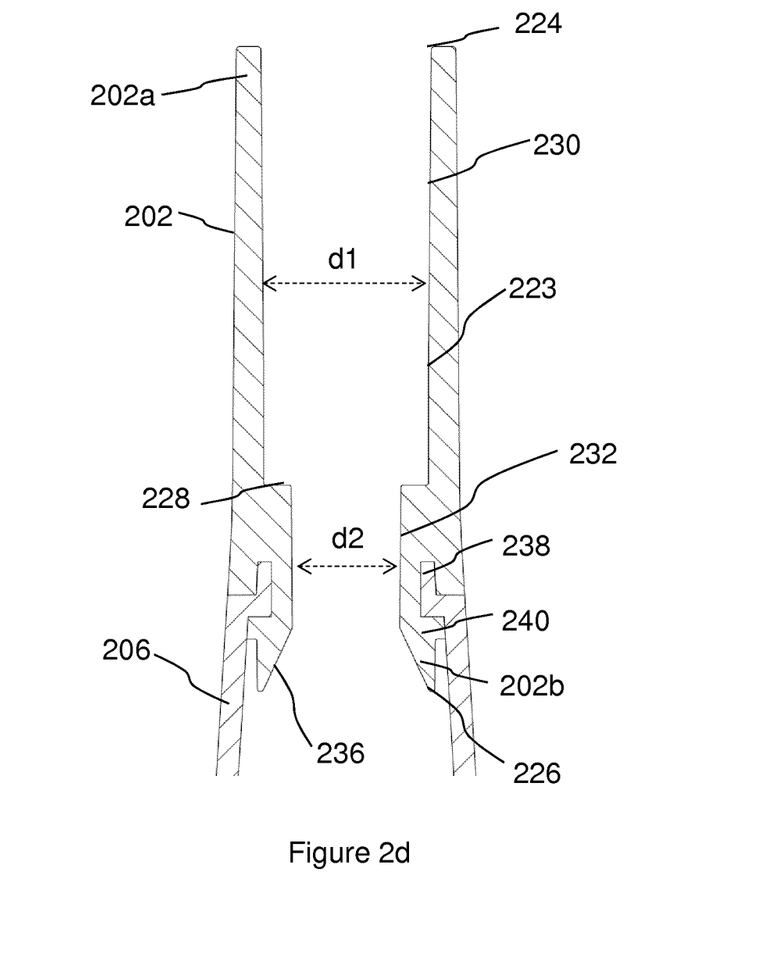
FIG. 2d shows a detail of the section of FIG. 2b with some elements removed for clarity.

FIGS. 2a to 2d illustrate a mouthpiece 202 according to a first example. Specifically, FIG. 2a illustrates a side view of the mouthpiece 202 and upper portion 206 of the outer body 218 of a device (100 in FIG. 1). In this first example, FIG. 2b illustrates a section through line P-P in FIG. 2a, FIG. 2c illustrates a plan view of that shown in FIG. 2a, and FIG. 2d shows a detail of the section of FIG. 2b with a flavor element 234 and a liquid container 222 removed for clarity.

In FIGS. 2a to 2d, the mouthpiece 202 is connected to a portion 206 of an outer body 218 of an overall device (100 in FIG. 1). The example mouthpiece 202, portion 206 of the outer body 218, and liquid container 222 in FIGS. 2a to 2d can be used, for example, in the device 100 of FIG. 1 instead of the mouthpiece 102, upper portion 106 of the outer body 118, and liquid container 122 respectively. For brevity, features in FIGS. 2a to 2d and the functioning thereof that are the same or similar to those features already described with reference to FIG. 1 are given similar reference numerals to as in FIG. 1 but increased by 100, and will not be described in detail again.

Referring now to FIGS. 2a to 2d, the mouthpiece 202 defines a hole or aperture 223 extending from a first opening 224 at a first end 202a of the mouthpiece 202 to a second opening 226 at an opposing end 202b of the mouthpiece 202. The mouthpiece 202 has received in the aperture 223 through the first opening 224 a flavor element 234 for imparting a flavor to a flow of at least one of a vapor and an aerosol that passes through the mouthpiece 202 in use. The flavor element 234 may be the same as or similar to the flavor element 134 as mentioned above with reference to FIG. 1. The aperture 223 has a first radial dimension d1 towards the first opening 224, and a second, smaller radial dimension d2 towards the second opening 226, thereby to prevent the flavor element 234 received in the aperture 223 through the first opening 224 from passing through to the second opening 226. A user may therefore, for example, insert a flavor element 234 into the aperture 223 through the first opening 224 of the mouthpiece 202 only to a certain and/or predefined extent.

The aperture 223 is a stepped bore 230, 232 comprising a first bore 230 having the first radial dimension d1 and a second bore 232 having the second radial dimension d2. The step 228 of the stepped bore 230, 232 prevents the flavor element 234 from passing into the second bore 232 and hence towards the second opening 226. The step 228 of the stepped bore 230, 232 also supports the flavor element 234 received in the first bore 230.

The cross section of the flavor element 234 and the cross section of the at least a portion of the first bore 230 (and the first opening 224) may be matched so as to allow easy receipt of the flavor element 234 into the first bore 230. For example, as is shown in FIGS. 2a to 2d, the first bore 230 is cylindrical so as to receive therein the cylindrical flavor element 234. The diameter of the flavor element 234 may be approximately equal to, for example slightly smaller than, the diameter d1 of the first bore 230 so as to ensure an easy fit of the flavor element 234 into the first bore 230. In other examples, the diameter of the flavor element 234 may be slightly larger than the diameter d1 of the first bore 230, for example to ensure a tight (snug) fit of the flavor element 234 into the first bore 230. In this case, the flavor element 234 may be or comprise a resilient and/or deformable material. The flavor element 234 may be retained in the mouthpiece 202 for example by friction with the walls of the mouthpiece 202 defining the first bore 230. The first radial dimension d1 may be, for example in the range of 7 to 9 millimeters, for example at or around 8 millimeters, for example 7.7 millimeters. The second radial dimension d2 may be, for example, in the range 4 to 6 millimeters, for example at or around 5 millimeters. The first bore 230 may be cylindrical, or may taper from the first opening 224 to the step 228. For example, the diameter of the first bore may taper from 7.8 millimeters at the first opening 224 to 7.5 millimeters at the step 228, for example. The diameter of the flavor element 234 may be, for example, in the range of 7 to 9 millimeters, for example at or around 8 millimeters, for example 7.64 mm.

In this first example, the first opening 224 is at a mouth end 202a of the mouthpiece 202, and the second opening 226 is at a device end 202b of the mouthpiece 202.

The flavor element 234 extends out beyond the first opening 224 of the mouthpiece 202. For example, the length of the first bore 230 from the first opening 224 to the step 228 may be at or around 11 millimeters, and the length of the flavor element may be at or around 22 millimeters, i.e. leaving 11 millimeters of rod extending beyond the first opening 224 of the mouthpiece 202, for example.

The flavor element 234 extending out beyond the first opening 224 of the mouthpiece 202 allows, for example, a user to draw on the flavor element 234 rather than on the mouthpiece 202. This may improve user experience, for example, because the flavor element 234 can be fabricated to have a diameter, for example between 7 and 9 millimeters (e.g. at or around 8 millimeters), more preferable for a user to place in their mouth. This may also improve user experience, for example, because the flavor element 234 can be fabricated to be made of or comprise a material more preferable for a user to place in their mouth, for example cellulose acetate and/or paper, for example coated paper. Moreover, this may improve hygiene because the user can dispose of and replace the flavor element 234, i.e. frequently replace (if desired) that part of the device 100 which comes into contact with their mouth. This may also make sharing of a single device between multiple users more attractive and/or convenient. Further, the flavor element 234 extending out beyond the first opening 224 of the mouthpiece 202 allows for the flavor element 234 to be easily removed from the mouthpiece 202, for example by a user manually pulling the flavor element 234 out of the first opening 224, for example against the friction between the flavor element 234 and the walls of the mouthpiece 202 defining the first bore 230. A user may do this, for example, when the flavor and/or other constituents of the flavor element 234 have expired or deteriorated. A replacement flavor element 234 can then be easily inserted, for example by a user holding the flavor element 234 and manually pushing it into the first bore 230 up until the flavor element abuts the step 228, for example.

The device end 202b of the mouthpiece 202 is arranged to be releasably connectable to the upper portion 206 of the outer body 218 of the device (100 in FIG. 1). The device end 202b of the mouthpiece 202 has a connecting element 240 for connecting with a reciprocal connecting element 238 of the upper portion 206 of the outer body 218. The connecting element 240 of the mouthpiece 202 comprises a protrusion 240 for snap-fitting against a ledge 238 of the upper portion 206 of the outer body 218. The mouthpiece 202 may be released from the portion 206 of the outer body 218 by a user manually squeezing the mouthpiece 202 across its width, thereby to disengage the protrusion 240 from the ledge 238, thereby allowing the user to lift the mouthpiece 202 out and away from the upper portion 206 of the outer body 218. It will be appreciated that any other releasable connecting elements and/or mechanism may be used. For example, the mouthpiece 202 may be releasably connected to the portion 206 of the outer body 218 by friction fit, push fit, screw fit e.g. using reciprocal threads etc. The mouthpiece 202 being releasably connectable to the outer body 218 allows for example a user to easily access the liquid container 222 and/or the second opening 226 of the mouthpiece 202 e.g. for cleaning purposes.

It will be appreciated that in some examples, the mouthpiece 202 and the upper portion 206 of the outer body 218 are not releasably connectable to one another. For example, the mouthpiece 202 and the upper portion 206 of the outer body 218 may be co-molded pieces that are not separable by a user. For example, the connecting element 240 of the mouthpiece 202 may be co-molded with the connecting element 238 of the upper portion 206 of the outer body 218. In this case, for example, in order for a user to access the liquid container 216, for example so as to remove and/or replace the liquid container 216 from the device (100 in FIG. 1), the user removes as one piece the mouthpiece 202 and the upper portion 206 of the outer body 218 from the lower portion (105 in FIG. 1) of the outer body 218 of the device (100 in FIG. 1).

The mouthpiece 202, at the opening 226 at the device end 202b of the mouthpiece 202, comprises a chamfer 236 for contacting the liquid container 222. The chamfer 236 extends all the way around the circumference of the second opening 226 of the mouthpiece 202. A rim 225 (i.e. an apex or corner 225) at the upper end 222a of the liquid container 222 may press against the chamfer 236 of the mouthpiece 202 in use thereby to form a seal between the liquid container 222 and the mouthpiece 202. This allows all or substantially all of the vapor or aerosol exiting a channel (not shown) in the liquid container 222 at the upper end 222a of the liquid container 222 in use to flow into the aperture 223 of the mouthpiece 202 and thereafter through the flavor element 234. The opening 226 at the device end 202b of the mouthpiece 202 is circular so as that a seal may be easily and reliably formed between the mouthpiece 202 and the circular rim 225 of the liquid container 222. It will be appreciated that in other examples, the mouthpiece 202 may not comprise such a chamfer 236. For example, a face (not shown) of the mouthpiece 202 at the device end 202b opening 226 may contact flush with a face of the liquid container 222 (i.e. in a head on arrangement) thereby to form a seal between the mouthpiece 202 and the liquid container 222. In another example, the mouthpiece 202, at the opening 226 at the device end 202b of the mouthpiece 202, may comprise alternatively or additionally a protruding circumferential wall or lip that contacts the liquid container 222, for example contacts an inner face of a corresponding protruding circumferential wall or lip at the rim 225 of the liquid container 222.

The upper portion 206 of the housing 218 comprises one or more second connecting elements 239 for releasably connecting the upper portion 206 of the housing 218 to the lower portion (105 in FIG. 1) of the housing 218. The second connecting elements 239 may be, for example, protrusions of the upper portion 206 for receipt into reciprocal recesses in the lower portion (105 in FIG. 1) of the housing 218. It will be appreciated that any releasable connecting elements or mechanism may be used instead, for example, friction fit, push fit, screw fit e.g. using reciprocal threads etc.

In use, when the upper portion 206 of the outer body 218 and liquid container 222 are connected to the rest of the device (e.g. as shown schematically for device 100 in FIG. 1), when a user draws on the flavor element 234, air is drawn in through an air inlet (120 in FIG. 1). A heater (110 in FIG. 1) volatilizes liquid 216 held in the liquid container 222 into the inlet air to generate a flow of vapor or aerosol. The flow passes through the channel (not shown) in the liquid container out of the upper end 222a of the liquid container 222, through the second bore 232, through the flavor element 234, and exits from an upper end 234a of the flavor element 234 for inhalation by the user. Where the flavor element 234 comprises one or more constituents, the flow of vapor or an aerosol through the flavor element 234 entrains one or more of the constituents in the flow.

Figure 3A:
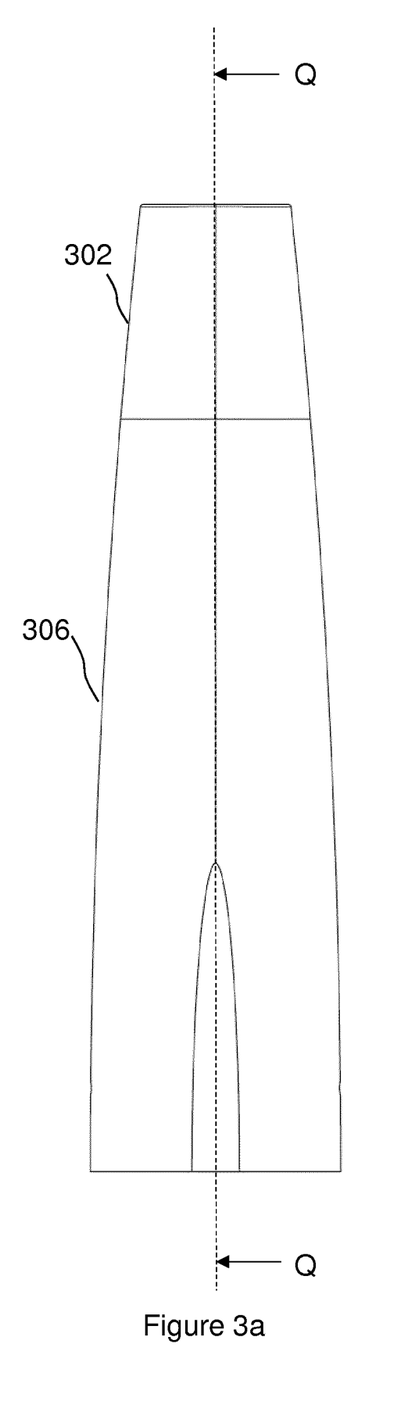
FIG. 3a shows a side view of an exemplary mouthpiece and portion of an apparatus for generating an inhalable medium.
Figure 3B:
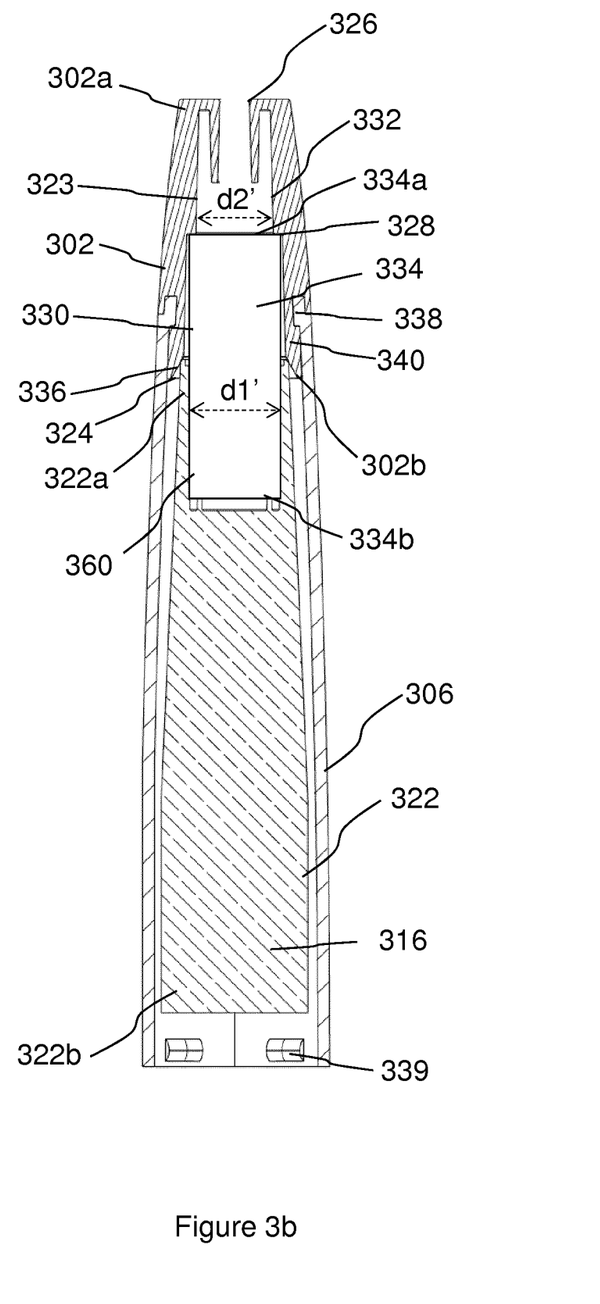
Figure 3C:
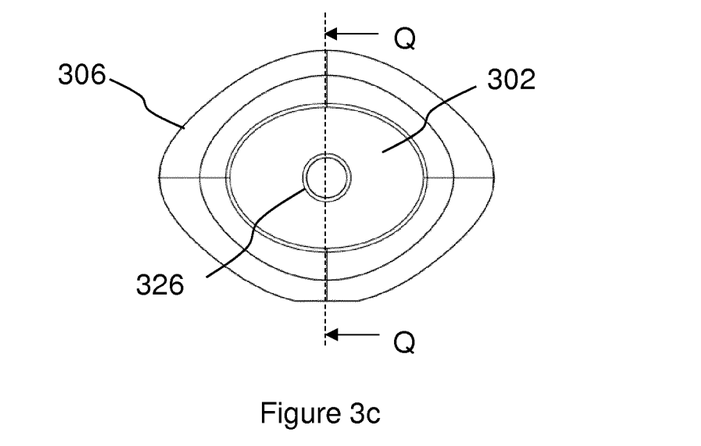
Figure 3D:
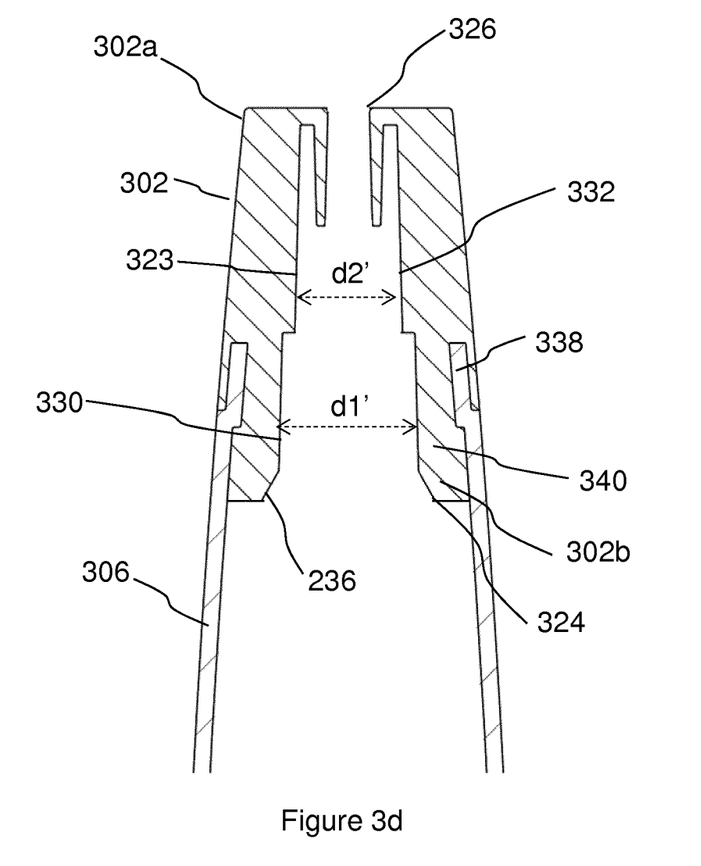
FIG. 3d shows a detail of the section of FIG. 3b with some elements removed for clarity.

FIGS. 3a to 3d illustrate a mouthpiece 302 according to a second example. Specifically, FIG. 3a illustrates a side view of the mouthpiece 302 and upper portion 306 of the outer body 318 of a device (100 in FIG. 1), FIG. 3b illustrates a section through line Q-Q in FIG. 3a, FIG. 3c illustrates a plan view of that shown in FIG. 3a, and FIG. 3d shows a detail of the section of FIG. 3b with a flavor element 334 and a liquid container 322 removed for clarity.

In FIGS. 3a to 3d, the mouthpiece 302 is connected to an upper portion 306 of an outer body 318 of an overall device (100 in FIG. 1). The example mouthpiece 302, portion 306 of the outer body 318, and liquid container 322 in FIGS. 3a to 3d can be used, for example, in the device 100 of FIG. 1 instead of the mouthpiece 102, portion 106 of the outer body 118, and liquid container 122 respectively. For brevity, features in FIGS. 3a to 3d and the functioning thereof that are the same or similar to those features already described with reference to FIGS. 1 to 2d are given similar reference numerals to as in FIGS. 2a to 2d but increased by 100, and will not be described in detail again.

Referring now to FIGS. 3a to 3d, the mouthpiece 302 defines a hole or aperture 323 extending from a first opening 324 at a first end 302b of the mouthpiece 302 to a second opening 326 at an opposing end 302a of the mouthpiece 302. In this second example, the first opening 324 is at a device end 302b of the mouthpiece 302, and the second opening 326 is at a mouth end 302a of the mouthpiece 302. The mouthpiece 302 has received in the aperture 323 through the first opening 324 a flavor element 334 for imparting a flavor to a flow of at least one of a vapor and an aerosol that passes through the mouthpiece 302 in use. The flavor element 334 may be similar to or the same as the flavor element 234 and/or 134 described above. The aperture 323 has a first radial dimension d1' towards the first opening 324, and a second, smaller radial dimension d2' towards the second opening 326, thereby to prevent the flavor element 334 received in the aperture 323 through the first opening 324 from passing through to the second opening 326. The flavor element 334 may therefore be held within the device (100 in FIG. 1) by the mouthpiece 302.

The aperture 323 comprises a stepped bore 330,332 comprising a first bore 330 having the first radial dimension d1' and a second bore 332 having the second radial dimension d2'. The step 328 of the stepped bore 330, 332 prevents the flavor element 334 from passing into the second bore 332 and hence towards the second opening 326. The cross section of the flavor element 334 and the cross section of at least a portion of the first bore 330 (and the first opening 324) may be matched so as to allow easy receipt of the flavor element 334 into the first bore 330. For example, as is shown in FIGS. 3a to 3d, the first bore 330 (and the first opening 324) is cylindrical so as to receive therein the cylindrical flavor element 334. The diameter of the flavor element 334 may be approximately equal to, for example slightly smaller than, the diameter d1' of the first bore 330 so as to ensure an easy fit of the flavor element 334 into the first bore 330. In other examples, the diameter of the flavor element 334 may be slightly larger than the diameter d1' of the first bore 330, for example to ensure a tight (snug) fit of the flavor element 334 into the first bore 330. In this case, the flavor element 334 may be or comprise a resilient and/or deformable material. The flavor element 334 may be retained in the mouthpiece 302, for example, by friction. The first radial dimension d1' may be, for example in the range of 7 to 9 millimeters, for example at or around 8 millimeters, for example 7.7 millimeters. The second radial dimension d2' may be, for example, in the range 4 to 6 millimeters, for example at or around 5 millimeters. The first bore 330 may be cylindrical, or may taper slightly from the first opening 324 to the step 328. For example, the diameter of the first bore may taper from 8.4 millimeters at the first opening 324 to 8.0 millimeters at the step 328, for example. The diameter of the flavor element 234 may be in the range of 7 to 9 millimeters, for example at or around 8 millimeters, for example 7.64 millimeters.

The flavor element 334 extends out (protrudes) beyond the first opening 324 of the mouthpiece 302. For example, this allows a user, when the mouthpiece 302 is disconnected from the upper portion 306 of the housing 318, to easily manually remove and/or replace the flavor element 324 in the first bore 330 (through the first opening 234) of the mouthpiece 302. For example, the length of the first bore 330 from the first opening 324 to the step 328 may be at or around 12 millimeters, and the length of the flavor element may be at or around 22 millimeters, i.e. leaving around 10 millimeters of rod extending beyond the first opening 224 of the mouthpiece 202, for example. In examples where the mouthpiece 302 and the upper portion 306 of the outer body 318 are not releasably connectable to one another, the user may remove as one piece the mouthpiece 302 and the upper portion 306 of the outer body 318 from the lower portion (105 in FIG. 1) of the outer body 318 of the device (100 in FIG. 1), thereby to expose the flavor element 304 to allow a user to easily remove and/or replace the flavor element 304.

The liquid container 322 comprises a recess 360 in the upper end 222a of the liquid container 322 into which a lower portion 334b of the flavor element 324 is received. The flavor element 324 extends out (protrudes) from the recess 360, out beyond the liquid container 332, so as to also be received in the first bore 330 of the mouthpiece 302 when the mouth piece 302 and the upper portion 306 of the outer body 318 are connected together. The cross section of the flavor element 334 and the cross section of the recess 360 may be matched so as to allow easy receipt of the flavor element 334 into the recess 360. For example, as is shown in FIGS. 3a to 3d, the recess 360 is cylindrical so as to receive therein the cylindrical flavor element 334. The diameter of the flavor element 334 may be approximately equal to, for example slightly smaller than, the diameter of the recess 360 so as to allow easy receipt of the flavor element 334 into the recess 360. In other examples, the diameter of the flavor element 334 may be slightly larger than the diameter of the recess 360, for example to ensure a tight (snug) fit of the flavor element 334 into the recess 360. In this case, the flavor element 334 may be or comprise a resilient and/or deformable material.

Similarly to as described above for the first example, the device end 302b of the mouthpiece 302 is arranged to be releasably connectable to the upper portion 206 of the outer body 318 of the device for example via connecting element 340 for connecting with a reciprocal connecting element 338 of the portion 306 of the outer body 318. As above, the connecting elements 340, 338 or connecting mechanism may comprise any releasable connection, for example, by snap fit, friction fit, push fit, screw fit e.g. using reciprocal threads etc.

The mouthpiece 302 being releasably connectable to the upper portion 306 of the outer body 318 allows a user for example to easily access the flavor element 324 that may be received in one of the bore 330 of the mouthpiece 302 and the recess 360 of the liquid container 322 when the mouthpiece 302 is removed from the upper portion 306 of the outer body 318. For example, a user may manually pull the flavor element 334 out of the first opening 324 of the mouthpiece 302 (or the recess 360 of the liquid container 322), for example against the friction between the flavor element 234 and the walls of the mouthpiece 202 defining the first bore 230 (or the walls of the liquid container 322 defining the recess 360). A user may do this, for example, when the flavor and/or other constituents of the flavor element 334 have expired or deteriorated. A replacement flavor element 334 can then be easily inserted, for example by a user holding an upper end 334a of the flavor element and pushing the lower end 334b of the flavor element 334 it into the recess 360 of the liquid container 322. The user may then lower the mouthpiece 302 over the upper end 334a of the flavor element 334 so that the flavor element 334 is received into the first bore 330 (through the first opening 324) of the mouthpiece 302. The user may then connect the mouthpiece 302 to the upper portion 306 of the outer body 318, at which point the upper end 334a of the flavor element 334 will be abutting or near abutting the step 328 of the stepped bore 330,332 of the mouthpiece 302. The flavor element 302 is therefore held securely in position between the mouthpiece 302 and the liquid container 322.

As above, it will be appreciated that in some examples, the mouthpiece 302 and the upper portion 306 of the outer body 318 are not releasably connectable to one another. For example, the mouthpiece 302 and the upper portion 306 of the outer body 318 may be co-molded pieces that are not separable by a user. For example, the connecting element 340 of the mouthpiece 302 may be co-molded with the connecting element 338 of the upper portion 306 of the outer body 318. In this case, for example, in order for a user to access the flavor element 304, for example so as to remove and/or replace the flavor element 304 from the recess 360 of the liquid container 322, the user removes as one piece the mouthpiece 302 and the upper portion 306 of the outer body 318 from the lower portion (105 in FIG. 1) of the outer body 318 of the device (100 in FIG. 1). A user may then, for example, manually pull the flavor element 334 out of the recess 360 of the liquid container 322, for example, when the flavor and/or other constituents of the flavor element 334 have expired or deteriorated, or the user wants to change the flavor of the aerosol or vapor produced. A replacement flavor element 334 can then be easily inserted, for example by a user holding an upper end 334a of the flavor element and pushing the lower end 334b of the flavor element 334 it into the recess 360 of the liquid container 322. The user may then lower the mouthpiece 302 and the upper portion 306 of the outer body 318, as one piece, over the upper end 334a of the flavor element 334 so that the flavor element 334 is received into the first bore 330 (through the first opening 324) of the mouthpiece 302. The user may then connect the upper portion 306 of the outer body 318 to the lower portion (105 in FIG. 1) of the outer body, at which point the upper end 334a of the flavor element 334 will be abutting or near abutting the step 328 of the stepped bore 330, 332 of the mouthpiece 302. The flavor element 302 is therefore held securely in position between the mouthpiece 302 and the liquid container 322.

In either case, the flavor element 334 extending into the recess 360 of the liquid container 332 and into the first bore 330 of the mouthpiece 302 allows for the flavor element 334 to be relatively long for example, and hence have the potential to impart more flavor and/or other constituents into the vapor or aerosol in use, but without the need to extend the length of the overall device (100 in FIG. 1).

As in the first example, the mouthpiece 303 may comprise, at the opening 326 at the device end 302b of the mouthpiece 302, a chamfer 336 for contacting a rim 335 at the upper end 322a of the liquid container 322, thereby to form a seal between the liquid container 322 and the mouthpiece 302.

As in the first example, the upper portion 306 of the housing 318 comprises one or more second connecting elements 339 for releasably connecting the portion 306 of the housing 318 to the lower portion (105 in FIG. 1) of the housing 318.

In use, when the portion 306 of the outer body 318 and liquid container 322 is connected to the rest of the overall device (e.g. as shown schematically for device 100 in FIG. 1), when a user draws on the mouth end 302a of the mouthpiece 302, air is drawn in through an air inlet (120 in FIG. 1). A heater (110 in FIG. 1) volatilizes liquid 316 held in the liquid container 322 into the inlet air to generate a flow of vapor or aerosol. The flow passes out of a channel (not shown) in the liquid container 322, out into the recess 360 of the liquid container, through the flavor element 334 so as to exit at the upper end of the flavor element 334a, out into the second bore 332 of the mouthpiece and out of the second opening 324 at the mouth end 302a of the mouthpiece 322 for inhalation by the user. Where the flavor element 334 comprises one or more constituents, the flow of vapor or an aerosol through the flavor element 334 entrains one or more of the constituents in the flow.

Figure 4A:
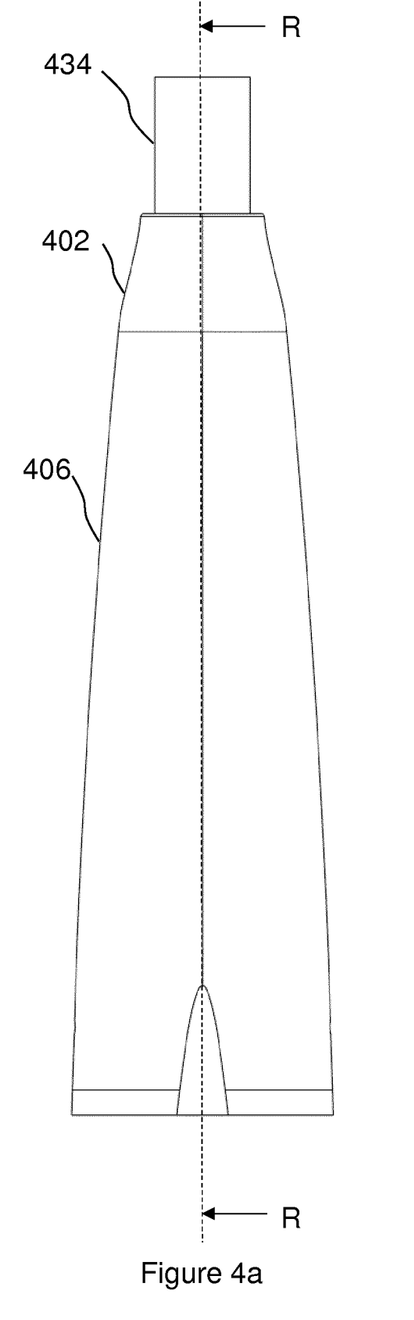
FIG. 4a shows a side view of an exemplary mouthpiece and portion of an apparatus for generating an inhalable medium.
Figure 4B:
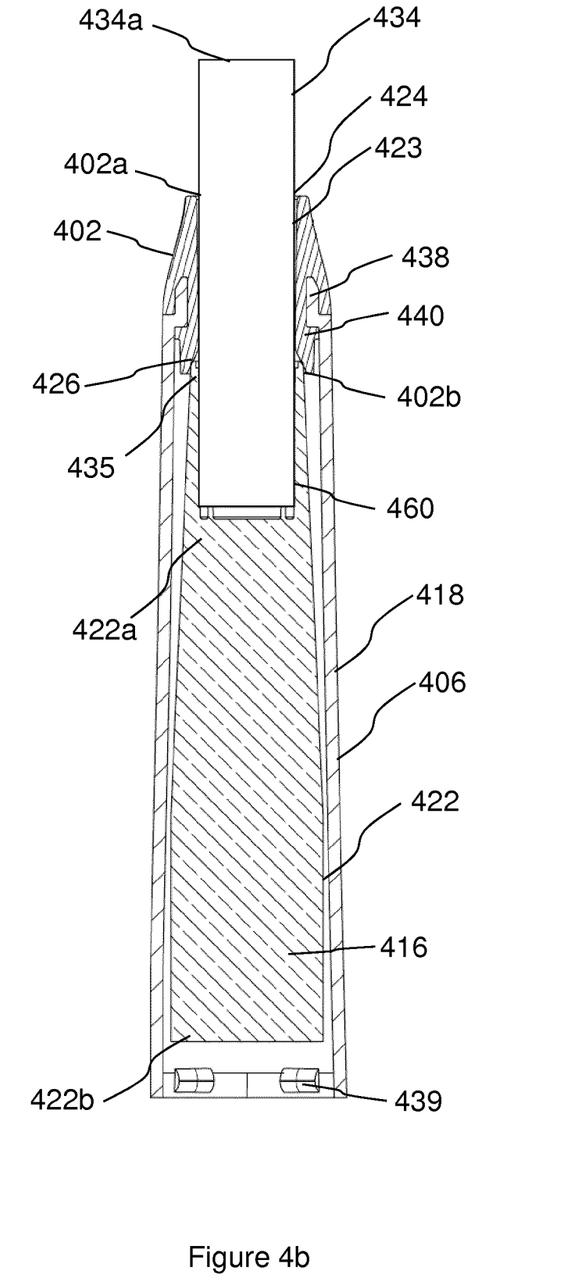
Figure 4C:
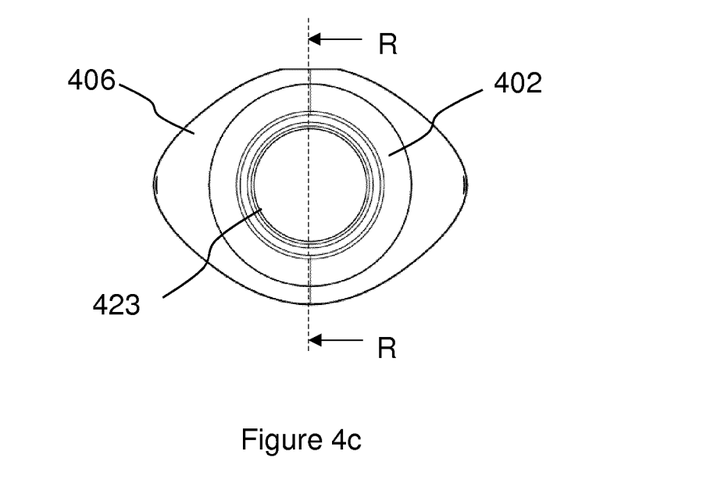
Figure 4D:
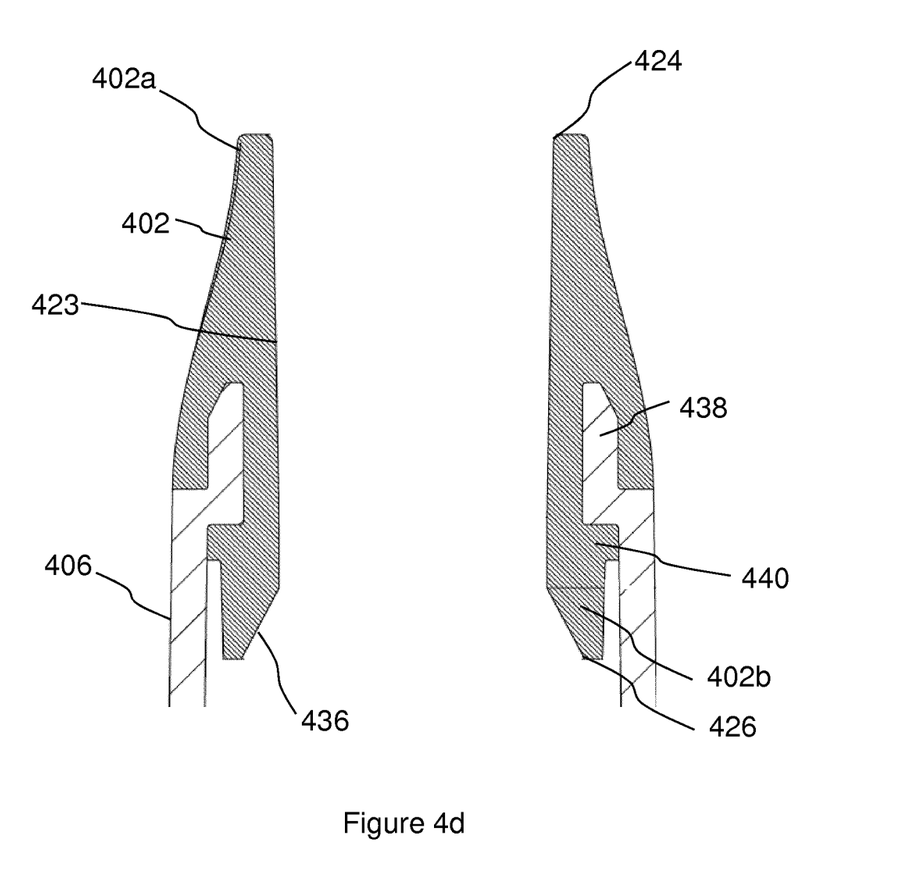
FIG. 4d shows a detail of the section of FIG. 4b with some elements removed for clarity.

FIGS. 4a to 4d illustrate a mouthpiece 402 according to a third example. Specifically, FIG. 4a illustrates a side view of the mouthpiece 402 and upper portion 406 of the outer body 418 of a device (100 in FIG. 1), FIG. 4b illustrates a section through line R-R in FIG. 4a, FIG. 4c illustrates a plan view of that shown in FIG. 4a, and FIG. 4d shows a detail of the section of FIG. 4b with a flavor element 434 and a liquid container 422 removed for clarity.

In FIGS. 4a to 4d, the mouthpiece 402 is connected to an upper portion 406 of an outer body 418 of an overall device (100 in FIG. 1). The example mouthpiece 402, upper portion 406 of the outer body 418, and liquid container 422 in FIGS. 3a to 3d can be used, for example, in apparatus 100 of FIG. 1 instead of the mouthpiece 102, upper portion 106 of the outer body 118, and liquid container 122 respectively. For brevity, features in FIGS. 4a to 4d and the functioning thereof that are the same or similar to those features already described with reference to as in FIGS. 1 to 3d are given similar reference numerals to as in FIGS. 3a to 3d but increased by 100, and will not be described in detail again.

Referring now to FIGS. 4a to 4d, the mouthpiece 402 defines a hole or aperture 423 extending from a first opening 424 at a mouth end 402a of the mouthpiece 422 to a second opening 426 at an opposing, device end 402b of the mouthpiece 422. The mouthpiece 422 has received in the aperture 423 through the first opening 424 a flavor element 434 for imparting a flavor to a flow of at least one of a vapor and an aerosol that passes through the mouthpiece 422 in use. The flavor element 434 may be similar to or the same as the flavor element 334 of the second example or the flavor element 234 of the first example described above. In this third example, the flavor element 434 extends out (protrudes) beyond the first opening 424 for receipt into a user's mouth, and extends out (protrudes) beyond the second opening 426 for contact with the liquid container 422 (example of a component of the device (100 in FIG. 1)). For example, the length of the flavor element may be at or around 36 millimeters, and the length of the aperture 423 from the first opening 424 to the second opening 426 may be at or around 11 millimeters, for example.

The cross section of the flavor element 434 and the cross section of the aperture 423 may be matched so as to allow easy receipt of the flavor element 434 into the aperture 423. For example, as is shown in FIGS. 4a to 4d, the aperture 434 is cylindrical so as to receive therein the cylindrical flavor element 434. The diameter of the flavor element 434 may be approximately equal to, for example slightly smaller than, the diameter of the aperture 434 so as to ensure an easy fit of the flavor element 434 into the aperture 434. In other examples, the diameter of the flavor element 434 may be slightly larger than the diameter of the aperture 434, for example to ensure a tight (snug) fit of the flavor element 434 into the aperture 434. In this case, the flavor element 434 may be or comprise a resilient and/or deformable material. The flavor element 434 may be retained in the aperture 434 by friction.

Similarly to as described in the second example, the liquid container 422 comprises a recess 460 in the upper end 422a of the liquid container 422 into which a lower portion 434b of the flavor element 424 is received. The flavor element 424 extends out (protrudes) beyond the recess 460 so as to also be received in the aperture 423 of the mouthpiece 402. The cross section of the flavor element 434 and the cross section of the recess 460 may be matched so as to allow easy receipt of the flavor element 434 into the recess 460. For example, as is shown in FIGS. 4a to 4d, the recess 460 is cylindrical so as to receive therein the cylindrical flavor element 434. The diameter of the flavor element 434 may be approximately equal to, for example slightly smaller than, the diameter of the recess 460 so as to ensure an easy fit of the flavor element 434 into the recess 460. In other examples, the diameter of the flavor element 434 may be slightly larger than the diameter of the recess 460, for example to ensure a tight (snug) fit of the flavor element 434 into the recess 460. In this case, the flavor element 434 may be or comprise a resilient and/or deformable material. The flavor element 343 may be retained in the recess 460 by friction for example. For example, the diameter of the aperture 434 may be in the range 7 to 9 millimeters, for example at or around 8 millimeters, for example 7.7 millimeters. The aperture 434 may be cylindrical, or may taper slightly from the first opening 424 to the second opening 426. For example, the diameter of the aperture 434 may taper from 7.9 millimeters at the first opening 424 to 7.5 millimeters at the second opening 426, for example. The diameter of the flavor element 234 may be in the range of 7 to 9 millimeters, for example at or around 8 millimeters, for example 7.64 millimeters.

Similarly to as described in the first example, the flavor element 434 extending out beyond the first opening 424 of the mouthpiece 402 allows, for example, a user to draw on the flavor element 434 rather than the mouthpiece 402. This allows, for example, a user to draw on the flavor element 434 alone. This may improve user experience, for example, because the flavor element 434 can have a diameter and/or be made of a material more preferable for a user to place in their mouth. Moreover, this may improve hygiene characteristics of the device (100 in FIG. 1) because the user can dispose of and replace the flavor element 434, i.e. frequently replace (if desired) that part of the device 100 which comes into contact with their mouth. Further, the flavor element 434 extending out beyond the first opening 424 of the mouthpiece 402 allows for the flavor element 234 to be easily removed from the mouthpiece 402, for example by a user manually pulling the flavor element 434 out of the recess 436 and the aperture 423 by the first opening 424, for example against the friction between the flavor element 434 and the walls of the mouthpiece 402 defining the aperture 434 and/or the walls of the liquid container 422 defining the recess 436. A user may do this, for example, when the flavor and/or constituents of the flavor element 434 have expired or deteriorated. A replacement flavor element 434 can then be easily inserted, for example by a user holding the flavor element 434 and pushing it through the first opening 424, through the aperture 423, and into the recess 460 of the liquid container 422 up until the flavor element 434 contacts the liquid container 422. The flavor element 434 extending out (protruding) beyond the second opening 426 of the mouthpiece 402 into the recess 460 of the liquid container 432 (and out beyond the first opening 424 of the mouthpiece 402) allows for the flavor element 434 to be relatively long, and hence have the potential to impart more flavor and/or other constituents into the vapor or aerosol in use, but without the need to extend the length of the overall device (100 in FIG. 1).

As in the first and second examples, the device end 402b of the mouthpiece 402 is arranged to be releasably connectable to the upper portion 406 of the outer body 418 of the device for example via connecting element 440 for connecting with a reciprocal connecting element 438 of the upper portion 406 of the outer body 418. As above, the connecting elements 440, 438 and/or connecting mechanism may comprise any releasable connection, for example, by snap fit, friction fit, push fit, screw fit e.g. using reciprocal threads etc. As above, it will be appreciated that in some examples, the mouthpiece 402 and the upper portion 406 of the outer body 418 are not releasably connectable to one another. For example, the mouthpiece 402 and the upper portion 406 of the outer body 318 may be co-molded pieces that are not separable by a user. For example, the connecting element 440 of the mouthpiece 402 may be co-molded with the connecting element 438 of the upper portion 306 of the outer body 418.

As in the first and second examples, the mouthpiece 402 may comprise, at the opening 426 at the device end 402b of the mouthpiece 402, a chamfer 436 for contacting a rim 435 at the upper end 422a of the liquid container 422, thereby to form a seal between the liquid container 422 and the mouthpiece 402.

As in the first and second examples, the upper portion 406 of the housing 418 comprises one or more second connecting elements 439 for releasably connecting the portion 406 of the housing 418 to the lower portion (105 in FIG. 1) of the housing 418.

In use, when the upper portion 406 of the outer body 418 and liquid container 422 is connected to the rest of the device (e.g. as shown schematically for device 100 in FIG. 1), when a user draws on the flavor element 434, air is drawn in through an air inlet (120 in FIG. 1). A heater (110 in FIG. 1) volatilizes liquid 416 held in the liquid container 422 into the inlet air to generate a flow of vapor or aerosol. The flow passes out of a channel (not shown) in the liquid container 422, out into the recess 460 of the liquid container, through the flavor element 434, and exits from an upper end 434a of the flavor element 434a for inhalation by the user. Where the flavor element 434 comprises one or more constituents, the flow of vapor or an aerosol through the flavor element 434 entrains one or more of the constituents in the flow.

In the above examples, the liquid container 122, 222, 322, 422 was annular in shape and defined a cylindrical channel (not shown in the figures) running through the length of the liquid container 122, 222, 322, 422. However, in other examples, the liquid container may not be annular in shape, and/or the cartridge 104 may comprise an outer shell that defines an annular channel between the liquid container and the outer shell through which vapor or aerosol may pass.

Although the examples above referred to use of a cartridge 104, it will be readily appreciated that there are many configurations of so called e-cigarettes (some of which not having cartridges as such, but rather, for example, refillable liquid containers integral to the device 100) and that the above examples may also be applied to these or other configurations.

Although the above examples referred to the flavor element being cylindrical or having a cylindrical portion to be received into a cylindrical hole aperture or bore of the mouthpiece and/or of the recess of the liquid container, it will be appreciated that the flavor element may have any shaped cross section (e.g. oval, square, polygonal), and the aperture of the mouthpiece, or a portion thereof, and/or the recess of the liquid container, or a portion thereof, may correspondingly have any shaped cross section Although in the above examples, the mouthpiece comprised, at an opening of an aperture at the device end of the mouthpiece, a chamfer for contacting the liquid container, this need not necessarily be the case. In other examples, the mouthpiece may not comprise such a chamfer. For example, a face of the mouthpiece at the device end opening may contact flush with a face of the liquid container (i.e. in a head on arrangement) thereby to form a seal between the mouthpiece and the liquid container. In another example, the mouthpiece, at the opening of the aperture at the device end of the mouthpiece, may comprise alternatively or additionally a protruding circumferential wall or lip that contacts the liquid container, for example contacts an inner face of a corresponding protruding circumferential wall or lip at the rim of the liquid container. In yet other examples, there may be no such seal between the liquid container and the mouthpiece. For example, in the first and third examples described above where the user can draw on the flavor element rather than the mouthpiece itself, there may be alternatively or additionally a seal between flavor element and the liquid container.

The liquid 116, 216, 316, 416 is preferably a liquid that is volatilizable at reasonable temperatures, preferably in the range of 100-300° C. or more particularly around 150-250° C., as that helps to keep down the power consumption of the apparatus with which the cartridge is used. Suitable materials include those conventionally used in e-cigarette devices, including for example propylene glycol and glycerol (also known as glycerine). Also as described in relation to the examples above, the flavor element may be or comprise a material that may be used to impart a flavor (or other constituent) to the aerosol or vapor produced from the liquid as the aerosol or vapor passes through the flavor element. For example, the material may comprise constituents that impart cooling sensations, heating sensations, neutriceutical benefits, stimulating benefits or produce or induce any other sensation or benefit in the user. The material may for example consist of or comprise tobacco. As the aerosol or vapor passes through and over the tobacco material, the aerosol or vapor entrains organic and other compounds or constituents from the tobacco material that lend tobacco its organoleptic properties, thus imparting the flavor to the aerosol or vapor as it passes to the mouthpiece. Materials other than tobacco may be used to impart different flavors to the aerosol or vapor stream. For example, materials other than tobacco may be blended with tobacco, or blends of other materials such as, for example, vanilla pods, star anise, mint leaves, other herbs, and the like. For example, flavorants could be included in the material or in the liquid or both. In the example where flavorants are included in both the flavor element and the liquid, the generated vapor or aerosol may be flavored with a first flavor, and the flavor element may impart a second flavor to the vapor or aerosol passing there through. The first flavor and the second flavor may be the same, in which case the flavor element may act so as to enhance the flavor of the vapor or aerosol passing there through. The first flavor and the second flavor may be different, in which case the flavor element may act so as to alter the flavor of the vapor or aerosol passing there through. The user may therefore easily customize the flavor of the vapor or aerosol exiting the device for inhalation.

In any of the examples described above, an apparatus controller may control operation of the apparatus as a whole. The controller for example may cause the heater to be powered as and when required and switch off the heater when heating is not required. Operation of the heater may be controlled so that the liquid and/or material of the flavor element is heated to an optimum temperature. Particular considerations include ensuring that the flavor element does not burn, ensuring that adequate vaporization of the liquid is achieved, ensuring that the vaporized liquid or aerosol is at an appropriate temperature to liberate compounds from the flavor element, and ensuring that the vapor or aerosol that reaches the user is at a comfortable and safe temperature. A puff detector, a device which is known per se, may be provided to signal to the controller when the heater needs to be energized. Alternatively or additionally, the user may control the apparatus via controls or an interface external to the overall apparatus (not shown), for example via radio control signals, or Bluetooth or the like from a separate control device, such as a smartphone or the like.

In use, the material of the flavor element may be heated by vapor or aerosol with a temperature higher than the temperature of the material. It will be appreciated that any temperature above ambient temperature of the material and/or above the ambient temperature of the device as a whole will improve release of constituents from the solid material.

In use, the liquid may be heated to a temperature of between around 100-300° C. or more particularly around 150° C. to 250° C. Suitable liquid materials 116, 216, 316, 416 include materials that provide volatilized components upon heating, typically in the form of an aerosol. Suitable materials that the flavor element may be or comprise include any tobacco-containing material and may, for example, include one or more of tobacco per se, different varieties of tobacco, tobacco derivatives, pelletized tobacco, extruded tobacco, expanded tobacco, reconstituted tobacco, ground tobacco, tobacco extract, homogenized tobacco or tobacco substitutes. In the case of tobacco, the material may be in the form of a rod of tobacco, a pod or plug of tobacco, loose tobacco, agglomerates, etc., and may be in relatively dry form or in relatively moist form for example. The tobacco may have been modified, for example chemically modified, for example had its pH modified so as to promote the release of selected constituents of the tobacco such as nicotine. Suitable solid materials may include other, non-tobacco, products, which, depending on the product, may or may not contain nicotine. A tobacco rod may be formed using a wrapping material.

As used herein, the terms "flavor" and "flavorant" may refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus *Mentha*), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, solid, or powder. For example, a liquid, oil, or other such fluid flavorant may be impregnated in a porous solid material so as to impart flavor and/or other properties to that porous solid material. As such, the liquid or oil is a constituent of the material in which it is impregnated.

The above embodiments are to be understood as illustrative examples of the invention. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. An apparatus for generating an inhalable medium, the apparatus comprising a mouthpiece comprising:
   an aperture extending from a first opening at a first end of the mouthpiece to a second opening at an opposing end of the mouthpiece, wherein the first opening is at a mouth end of the mouthpiece and the second opening is at an apparatus end of the mouthpiece, the mouthpiece being arranged to receive in the aperture through the first opening a flavor element for imparting a flavor to a flow of at least one of a vapor or an aerosol that passes through the mouthpiece in use, the aperture having a first radial dimension towards the first opening and a second radial dimension towards the second opening, wherein the second radial dimension is smaller than the first radial dimension, and the flavor element for imparting a flavor to a flow of at least one of a vapor or an aerosol that passes through the mouthpiece in use, wherein the flavor element is received in the aperture of the mouthpiece through the first opening, wherein the flavor element protrudes beyond the first opening.

2. The apparatus of claim 1, wherein the aperture is or comprises a stepped bore, the stepped bore comprising a first bore portion having the first radial dimension and a second bore portion having the second radial dimension.

3. The apparatus of claim 1, wherein the mouthpiece comprises, at the second opening, a chamfer for engaging with a component of the apparatus.

4. The apparatus for generating an inhalable medium of claim 1, further comprising:
 a container for holding a liquid; and
 a heater for volatilizing liquid held in the container to generate the flow of at least one of a vapor or an aerosol in use;
 wherein in use the flow of the at least one of the vapor or the aerosol passes through the flavor element for inhalation by a user.

5. The apparatus of claim 4, wherein the container for holding liquid comprises a recess into which the flavor element is received.

6. The apparatus of claim 1, wherein the apparatus end of the mouthpiece is arranged to be releasably connected to the apparatus.

7. The apparatus of claim 1, further comprising a wall and wherein the flavor element engages the wall and the wall surrounds the flavor element.

8. The apparatus of claim 1, wherein the flavor element comprises nicotine.

9. The apparatus of claim 1, wherein the flavor element comprises tobacco.

10. The apparatus of claim 9, wherein the flavor element comprises a rod or plug of tobacco.

11. The apparatus of claim 1, wherein the flavor element comprises a material wrapped partially or wholly in a wrapper.

12. An apparatus for generating an inhalable medium, the apparatus comprising a mouthpiece comprising:
 an aperture extending from a first opening at a first end of the mouthpiece to a second opening at an opposing end of the mouthpiece, wherein the first opening is at a mouth end of the mouthpiece and the second opening is at an apparatus end of the mouthpiece, the mouthpiece being arranged to receive in the aperture through the first opening a flavor element for imparting a flavor to a flow of at least one of a vapor or an aerosol that passes through the mouthpiece in use, the aperture having a first radial dimension towards the first opening and a second radial dimension towards the second opening, wherein the second radial dimension is smaller than the first radial dimension,
 a container for holding a liquid; and
 a heater for volatilizing liquid held in the container to generate the flow of at least one of a vapor or an aerosol in use, and
 the flavor element for imparting a flavor to a flow of at least one of a vapor or an aerosol that passes through the mouthpiece in use, wherein the flavor element is received in the aperture of the mouthpiece through the first opening,
 wherein in use the flow of the at least one of the vapor or the aerosol passes through the flavor element for inhalation by a user, and
 wherein the container for holding liquid comprises a recess into which the flavor element is received.

* * * * *